(12) United States Patent
Kim et al.

(10) Patent No.: US 6,579,517 B1
(45) Date of Patent: *Jun. 17, 2003

(54) COSMETIC PRODUCT

(75) Inventors: Son Nguyen Kim, Hemsbach (DE); Axel Sanner, Frankenthal (DE); Volker Schehlmann, Schifferstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,534

(22) PCT Filed: May 12, 1999

(86) PCT No.: PCT/EP99/03295
§ 371 (c)(1),
(2), (4) Date: Nov. 2, 2000

(87) PCT Pub. No.: WO99/58100
PCT Pub. Date: Nov. 18, 1999

(30) Foreign Application Priority Data

May 14, 1998 (DE) ......................... 198 21 731

(51) Int. Cl.$^7$ .................. A61K 7/06; A61K 6/00; A61K 9/14; A61K 47/30; C08L 75/00; C08F 20/00

(52) U.S. Cl. .................. 424/70.12; 424/70.1; 424/401; 424/486; 524/591; 525/439; 514/772.3

(58) Field of Search .................. 424/70.12, 70.1, 424/401, 486; 524/591; 525/439; 514/772.3

(56) References Cited

U.S. PATENT DOCUMENTS

| | | | | |
|---|---|---|---|---|
| 4,336,358 A | * | 6/1982 | Alberts et al. | 525/439 |
| 4,486,577 A | * | 12/1984 | Mueller et al. | 525/474 |
| 4,567,228 A | | 1/1986 | Gaa et al. | 524/588 |
| 4,582,873 A | | 4/1986 | Gaa et al. | 524/591 |
| 4,743,673 A | | 5/1988 | Johnston et al. | 528/60 |
| 4,839,443 A | | 6/1989 | Akutsu et al. | 545/474 |
| 5,166,276 A | | 11/1992 | Hayama et al. | 525/329 |
| 5,169,641 A | * | 12/1992 | Jorda et al. | 424/486 |
| 5,334,372 A | | 8/1994 | Kawamata et al. | 424/78 |
| 5,417,967 A | | 5/1995 | Kawamata et al. | 424/78 |
| 5,472,686 A | | 12/1995 | Tsubaki et al. | 424/59 |
| 5,618,524 A | | 4/1997 | Bolich, Jr. et al. | 424/70 |
| 5,626,840 A | | 5/1997 | Thomaides et al. | 424/70 |
| 5,643,581 A | | 7/1997 | Mougin et al. | 424/401 |
| 5,650,159 A | * | 7/1997 | Lion et al. | 424/401 |
| 5,660,819 A | | 8/1997 | Tsubaki et al. | 424/70 |
| 5,939,491 A | * | 8/1999 | Wilt et al. | 525/100 |
| 5,997,853 A | | 12/1999 | Bolich, Jr. et al. | 424/70 |
| 6,093,384 A | | 7/2000 | Lion et al. | 424/45 |
| 6,277,386 B1 | * | 8/2001 | Kim et al. | 424/401 |

FOREIGN PATENT DOCUMENTS

| | | |
|---|---|---|
| CA | 2011246 | 9/1990 |
| CA | 2140665 | 2/1994 |
| CA | 2148805 | 6/1994 |
| CA | 2189886 | 5/1997 |
| DE | 195 41 326 | 5/1997 |
| DE | 195 41 329 | 5/1997 |
| EP | 0 017 122 | 10/1980 |
| EP | 0 729 742 | 9/1996 |
| JP | 5-295078 | 11/1993 |
| WO | WO 93/03703 | 3/1993 |
| WO | WO 94/03515 | 2/1994 |
| WO | WO 97/17052 | 5/1997 |
| WO | WO 97/17386 | 5/1997 |
| WO | WO 97/25021 | 7/1997 |

OTHER PUBLICATIONS

Derwent Abstracts, abstract No. 93–392731/49, abstract of JP 05 295 078, date =1993.*
Derwent Abstracts, abstract No. 75436, abstract of DE 2 912 484, date = 1980.*
Derwent Abstracts, abstract No. 96–394869/40, abstract of EP 729 742, date = 1996.*
Derwent Abstracts, abstract No. 97–260453/24, abstract of DE 19 541 329, date = 1997.*
Derwent Abstracts, abstract No. 97–260452/24, abstract of DE 19 541 326, date = 1997.*

* cited by examiner

Primary Examiner—Theodore J. Criares
Assistant Examiner—Michael A. Willis
(74) Attorney, Agent, or Firm—Keil & Weinkauf

(57) ABSTRACT

The present invention relates to a cosmetic composition which comprises at least one crosslinked, water-soluble or water-dispersible polyurethane formed from A) at least one polyurethane prepolymer having terminal isocyanate groups, and B) at least one polymer having isocyanate-reactive groups selected from hydroxyl, primary and secondary amino and/or carboxyl groups, at least one of components A) and/or B) being soluble or dispersible in water and at least one of components A) and/or B) comprising at least one siloxane group, and the salts thereof.

13 Claims, No Drawings

COSMETIC PRODUCT

This application is a 371 of PCT/EP99/03295 filed May 12, 1999.

The present invention relates to a cosmetic composition which comprises at least one crosslinked, water-soluble or water-dispersible polyurethane formed from at least one polyurethane prepolymer having terminal isocyanate groups and from at least one polymer having groups which are reactive toward isocyanate groups (isocyanate-reactive groups).

In cosmetology, polymers with film-forming properties are used for setting, shaping and improving the structure of the hair. These hair treatment compositions generally include a solution of the film former in an alcohol or in a mixture of alcohol and water.

Hairsetting compositions are generally sprayed onto the hair in the form of aqueous-alcoholic solutions. Following the evaporation of the solvent, the individual hairs are held in the desired shape at their points of mutual contact by the polymer which is left behind. The polymers should on the one hand be sufficiently hydrophilic that they can be washed out of the hair, yet on the other hand should be hydrophobic so that the hair treated with the polymers retains its shape even under conditions of high atmospheric humidity and the individual hairs do not stick to one another. In order to obtain a highly efficient hairsetting effect, moreover, it is also desirable to employ polymers which have a relatively high molecular weight and a relatively high glass temperature (at least 15° C.).

A further consideration when formulating hairsetting agents is that because of the environmental regulations governing the emission of volatile organic compounds (VOCs) into the atmosphere it is necessary to reduce the content of alcohol and of propellant.

A further current demand on hair treatment compositions is that they should give the hair a natural appearance and luster even, for example, when the hair concerned is by its very nature particularly vigorous and/or dark.

It is known to employ polysiloxanes, such as polydimethylsiloxane, and polysiloxane derivatives in haircare compositions.

EP-A-017 122 describes the use of polysiloxane-ammonium derivatives in hair washing and hair treatment compositions for improving the combability, softness and body of the hair.

EP-A-729 742 describes hair treatment compositions based on A) an amino-modified silicone terpolymer and B) at least one cationic, silicone-free conditioning agent based on a quaternary ammonium salt.

A disadvantage of the use, described in the two above-mentioned publications, of polysiloxanes which are not bonded covalently to the setting polymer is that there are frequent instances of separation of the formulations in the course of storage and following their application to the hair.

EP-A-408 311 describes the use of copolymers comprising units of a) ethylenically unsaturated, hydrophilic monomers and b) ethylenically unsaturated monomers with polysiloxane groups in haircare products.

EP-A-412 704 describes a haircare composition based on a graft copolymer which has monovalent siloxane polymer units on a backbone which is based on a vinyl polymer. After drying, the polymer breaks down into a discontinuous, silicone-containing phase and a continuous, silicone-free phase.

WO 93/03703 describes a hairspray composition comprising: a) from 0.1 to 2% by weight of a surface-active agent, b) from 0.5 to 15% by weight of an ionic resin having an number-average molecular weight of at least 300,000, and c) a liquid vehicle. In this case the ionic resin comprises silicone-containing monomers and, after drying, breaks down into a discontinuous, silicone-containing phase and a silicone-free continuous phase.

EP-A-362 860 describes alcohol-modified silicone ester derivatives and cosmetic compositions comprising them.

None of these publications describes setting polymers based on polyurethanes having a covalent bond of the siloxane groups to the setting polymers via nitrogen-containing groups. In particular, there is no description of crosslinked, water-soluble or water-dispersible polyurethanes which comprise siloxane groups. In addition, the suitability of such polymers for preparing low-VOC formulations is extremely limited.

Owing to their film-forming properties and generally low viscosity in water/ethanol, it is known in cosmetics to employ polyurethanes which are dispersible or soluble in water. For instance, U.S. Pat. No. 4,743,673 describes hydrophilic polyurethane polymers with carboxyl groups in the polymer backbone. These carboxyl groups are generated by hydrolyzing ester groups attached to the polymer backbone by from 30 to 60 minutes of heating with a strong base. This causes hydrolysis not only of the ester groups of the carboxylic ester component but also of those in the polyurethane chain. As a result, the polyurethane chain is cleaved and there is a drastic reduction in the molecular weight of the polyurethanes. Admittedly, there is a mention of the use of the polyurethanes in hairsprays, although in practice the films obtained with these polyurethanes cannot be used for hair cosmetics since they are either insoluble in water or have too low a molecular weight and hence an inadequate setting effect.

DE-A-42 25 045 and WO 94/03515 describe the use of water-soluble or water-dispersible anionic polyurethanes as hairsetting agents. These polyurethanes are synthesized from a) at least one compound containing two or more active hydrogen atoms per molecule, b) at least one diol which contains acid groups or salt groups, and c) at least one diisocyanate.

In terms of their elasticity, hairsetting polymers based on these polyurethanes are in need of improvement and generally lack a pleasant feel in the absence of additives.

DE-A-42 41 118 describes the use of noncrosslinked, cationic polyurethanes and polyureas as auxiliaries in cosmetic and pharmaceutical formulations.

EP-A-619 111 describes the use of polyurethanes based on organic diisocyanates, diols and 2,2-hydroxymethyl-substituted carboxylates of the formula

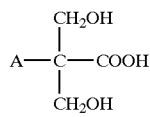

where A is a hydrogen atom or a $C_1$–$C_{20}$-alkyl group in hair fixatives. In this case at least some of the carboxyl groups are neutralized with an organic or inorganic base. Films based on these polyurethanes are soft and tacky, and the hairsetting compositions based thereon, correspondingly, are in need of improvement.

The polyurethanes described in the latter publications can go only part-way toward meeting the requirements made of hairsetting polymers. For instance, with all of the above-mentioned polyurethane-based products the desired sleekness of the hair is in need of improvement.

EP-A-636 361 describes a cosmetic composition comprising, in a cosmetically compatible vehicle, at least one pseudolatex based on a polycondensate which comprises at least one polysiloxane unit and at least one polyurethane and/or polyurea unit having anionic or cationic groups. There is no description of crosslinked, water-soluble or water-dispersible polyurethanes. The disclosure content of WO 97/25021 is similar. These cosmetic compositions are suitable, inter alia, for treating keratinous materials. The ease of washout of these film formers, however, is unsatisfactory. In addition, their high siloxane content robs them of the setting effect also required of a hair polymer.

DE-A-195 41 329 and WO 97/17052 describe hair treatment compositions comprising a salt which is dispersible or soluble in water and has the formula I

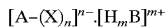

where

A is a cosmetically acceptable aliphatic, cycloaliphatic or aromatic radical, which may have siloxane-containing units and/or fluorine-containing units, X is a carboxylate, sulfonate, phosphate or phosphonate group;

B is a cosmetically acceptable amine base which may comprise siloxane-containing and/or fluorine-containing units;

n is from 1 to 30; and m is the valence of the amine B.

Hairspray formulations based on these siloxane-containing salts, on a hairsetting polymer which does not contain siloxane and on a silicone oil lead to films which are easily removed from the surface of the hair by mechanical stress, for example. The setting effect of these formulations is therefore in need of improvement.

DE-A-195 41 326 and WO 97/17386 describe water-soluble or water-dispersible polyurethanes having terminal acid groups, their preparation and their use. In this case a polyurethane prepolymer which is dispersible or soluble in water and has terminal isocyanate groups is reacted with an aminosulfonic or aminocarboxylic acid, especially taurine, aspartic acid and glutamic acid. Hairsprays based on these polyurethanes are still in need of improvement. Problems may occur in particular when formulating hairsprays having a high content of propellant gas and/or a high content of organic solvents and, possibly, with the simultaneous use of spray atomizers for obtaining very small droplets.

EP-A-492 657 describes a cosmetic composition for use in skincare and haircare products which comprises a linear polysiloxane-polyoxyalkylene block copolymer as repeating unit. Crosslinked, water-soluble or water-dispersible polyurethanes based on a siloxane-containing or siloxane-free polyurethane prepolymer are not described in this document.

EP-A-277 816 describes polydimethylsiloxanes having two hydroxyl groups at one chain end and a trimethylsilyl group at the other end, of the formula

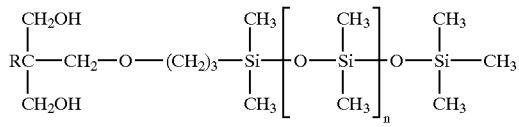

where R is hydrogen, methyl or ethyl and n is from 0 to 4000, and polyurethanes modified therewith. The resulting polyurethanes are exclusively modified polyurethanes of the type of a graft copolymer with siloxane-containing side chains and a polyurethane backbone. The use of these modified polyurethanes in hair cosmetics is not described.

EP-A-0 389 386 describes linear diorganopolysiloxane-polyester block copolymers having incorporated urethane units, which are suitable for the controlled release of pharmaceutical formulations.

EP-A-0 687 459 describes hair treatment compositions based on an aqueous polymer dispersion which is obtainable by free-radical graft copolymerization of a monoethylenically unsaturated siloxane macromonomer and at least one polyurethane and/or polyurea copolymer. Crosslinked polyurethanes formed from polyurethane prepolymers having terminal isocyanate groups and polymers having isocyanate-reactive groups are not described in this document.

EP-A-0 773 246 describes water-soluble or water-dispersible graft polymers composed of A) a water-soluble or water-dispersible polyurethane prepolymer having terminal isocyanate groups, and B) a protein which contains free amino groups.

These polymers are suitable as auxiliaries in cosmetics and, in particular as hairsetting agents having improved ease of washout. Disadvantages of using proteins is that they require stabilization by preservatives and, as natural substances, exhibit frequently fluctuating product properties.

It is an object of the present invention to provide new cosmetic compositions, especially polyurethane-based hair treatment compositions, which firstly can be used as hairsetting agents and secondly possess great ease of washout (redispersibility). They should preferably impart smoothness and sleekness to the hair.

We have found that this object is achieved by cosmetic compositions which comprise at least one crosslinked, water-soluble or water-dispersible polyurethane which is the product of reaction of at least one polyurethane prepolymer having terminal isocyanate groups and of at least one polymer having isocyanate-reactive groups, at least one of the components comprising a siloxane group.

The present invention therefore provides a cosmetic composition comprising at least one crosslinked, water-soluble or water-dispersible polyurethane formed from A) at least one polyurethane prepolymer having terminal isocyanate groups, and B) at least one polymer having isocyanate-reactive groups selected from hydroxyl, primary and secondary amino and/or carboxyl groups, at least one of components A) and/or B) being soluble or dispersible in water and at least one of components A) and/or B) comprising at least one siloxane group, and the salts thereof.

Polyurethane Prepolymer A)

Component A) is preferably a polyurethane prepolymer formed from a) at least one compound having a molecular weight in the range from 56 to 300 which comprises two active hydrogen atoms per molecule, b) at least one polymer having two active hydrogen atoms per molecule, c) if desired, a polysiloxane, d) if desired, at least one compound which has two active hydrogen atoms and at least one ionogenic or ionic group per molecule, e) at least one diisocyanate.

Component a) preferably comprises diols, diamines, amino alcohols, and mixtures thereof. The molecular weight of these compounds lies preferably within a range from about 56 to 280. If desired, up to 3 mol % of these compounds can be replaced by triols or triamines.

It is preferred as component a) to employ diols. Examples of diols which can be used are ethylene glycol, propylene glycol, butylene glycol, neopentyl glycol, cyclohexanedimethylol, di-, tri-, tetra-, penta- or hexaethylene glycol and mixtures thereof. Preference is given to the use of neopentyl glycol and/or cyclohexanedimethylol.

Examples of suitable amino alcohols are 2-aminoethanol, 2-(N-methylamino)ethanol, 3-aminopropanol, 4-aminobutanol, 1-ethylaminobutan-2-ol, 2-amino-2-methyl-1 propanol, 4-methyl-4-aminopentan-2-ol, etc.

Examples of suitable diamines are ethylenediamine, propylenediamine, 1,4-diaminobutane, 1,5-diaminopentane and 1,6-diaminohexane, and also α,ω-diaminopolyethers preparable by amination of polyalkylene oxides with ammonia.

Component b) is preferably a polymer having a number-average molecular weight in the range from about 300 to 5000, preferably from about 400 to 4000 and, in particular, from 500 to 3000. Useful polymers b) are, for example, polyesterdiols, polyetherols and mixtures thereof. Polyetherols are preferably polyalkylene glycols, examples being polyethylene glycols, polypropylene glycols, polytetrahydrofurans, etc., block copolymers of ethylene oxide and propylene oxide, or block copolymers of ethylene oxide, propylene oxide and butylene oxide which comprise the alkylene oxide units copolymerized in random distribution or in the form of blocks. It is preferred as component b) to employ polytetrahydrofurans, polyesterdiols and mixtures thereof.

Suitable polytetrahydrofurans b) can be prepared by cationic polymerization of tetrahydrofuran in the presence of acidic catalysts, such as sulfuric or fluorosulfuric acid, for example. Preparation techniques of this kind are known to the skilled worker.

Useful polyesterdiols b) preferably have a number-average molecular weight in the range from about 400 to 5000, more preferably from 500 to 3000 and, in particular, from 600 to 2000.

Suitable polyesterdiols are all those which are normally employed to prepare polyurethanes, especially those based on aromatic dicarboxylic acids, such as terephthalic, isophthalic, phthalic, Na- or K-sulfoisophthalic acid, etc., on aliphatic dicarboxylic acids, such as adipic or succinic acid, etc., and on cycloaliphatic dicarboxylic acids, such as 1,2-, 1,3- or 1,4-cyclohexanedicarboxylic acid. Particularly suitable diols are aliphatic diols, such as ethylene glycol, propylene glycol, 1,6-hexanediol, neopentyl glycol, diethylene glycol, polyethylene glycols, polypropylene glycols, 1,4-dimethylolcyclohexane, and also poly(meth)acrylatediols of the formula

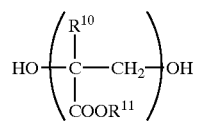

where $R^{10}$ is H or $CH_3$ and $R^{11}$ is $C_1$–$C_{18}$-alkyl (especially $C_1$–$C_{12}$- or $C_1$–$C_8$-alkyl) and which have a molecular mass of up to about 3000. Diols of this kind can be prepared by conventional means and are obtainable commercially (Tegomer® grades MD, BD and OD from Goldschmidt).

Preference is given to polyesterdiols based on aromatic and aliphatic dicarboxylic acids and aliphatic diols, especially those in which the aromatic dicarboxylic acid accounts for from 10 to 95 mol %, in particular from 40 to 90 mol % and, preferably, from 50 to 85 mol % of the overall dicarboxylic acid component (the remainder being aliphatic dicarboxylic acids).

Particularly preferred polyesterdiols are the reaction products of phthalic acid/diethylene glycol, isophthalic acid/1,4-butanediol, isophthalic acid/adipic acid/1,6-hexanediol, 5-$NaSO_3$-isophthalic acid/phthalic acid/adipic acid/1,6-hexanediol, adipic acid/ethylene glycol, isophthalic acid/adipic acid/neopentyl glycol, isophthalic acid/adipic acid/neopentyl glycol/diethylene glycol/dimethylolcyclohexane, and 5-$NaSO_3$-isophthalic acid/isophthalic acid/adipic acid/neopentyl glycol/diethylene glycol/dimethylolcyclohexane.

The polysiloxanes a) preferably comprise a compound of the formula I

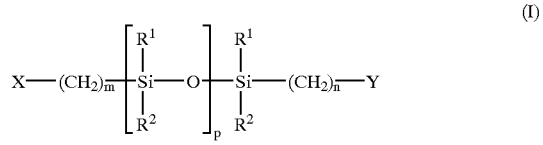

where $R^1$ and $R^2$ independently of one another are $C_1$- to $C_4$-alkyl, benzyl or phenyl, X and Y independently of one another are OH or $NHR^3$, where $R^3$ is hydrogen, $C_1$- to $C_6$-alkyl or $C_5$- to $C_8$-cycloalkyl, m and n independently of one another are from 2 to 8, and p is from 3 to 50.

Examples of suitable alkyl radicals are methyl, ethyl, n-propyl, isopropyl, n-butyl, t-butyl, n-pentyl, n-hexyl etc. Examples of suitable cycloalkyl radicals are cyclopentyl, cyclohexyl, cycloheptyl, cyclooctyl, etc.

$R^1$ and $R^2$ are preferably both methyl.

These polysiloxanes c) preferably have a number-average molecular weight in the range from about 300 to 5000, preferably from 400 to 3000.

Other suitable compounds c) are the polydimethylsiloxanes described in EP-A-227 816, incorporated herein by reference.

Suitable compounds d), which have two active hydrogen atoms and at least one ionogenic or ionic group per molecule, are, for example, compounds having carboxylate and/or sulfonate groups. Particular preference is given as component d) to dimethylolpropanoic acid and mixtures comprising it.

Examples of suitable diamines and/or diols d) having ionogenic or ionic groups are dimethylolpropanoic acid and compounds of the formula

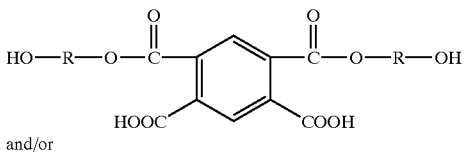

and/or

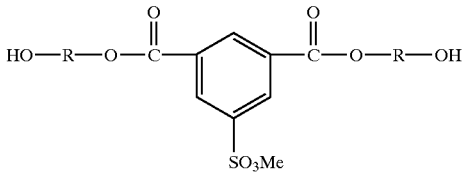

where each R is a $C_2$–$C_{18}$-alkylene group and Me is Na or K.

As component d) it is also possible to use compounds of the formulae

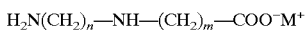

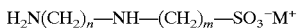

where m and n independently of one another are an integer from 1 to 8, in particular from 1 to 6, and M is Li, Na or K, and compounds of the formula

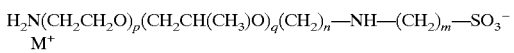

where m, n and M are as defined above, p and q independently of one another are an integer from 0 to 50, and at least one of the two variables, p or q, is >0. The sequence of the alkylene oxide units in this formula is arbitrary. The latter compounds preferably have a number-average molecular weight in the range from about 400 to 3000.

If compounds having nitrogen-containing groups are employed as component d), cationic polyurethanes are obtained. Examples of components d) which can be used are compounds of the formulae

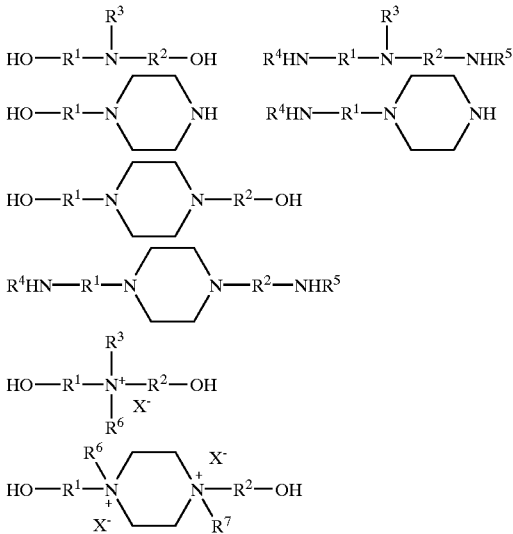

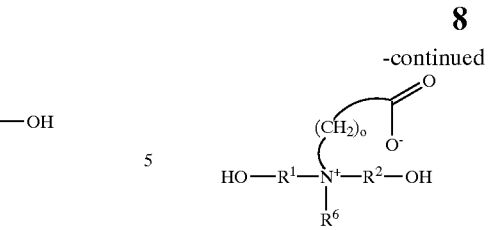

where $R^1$ and $R^2$, which can be identical or different, are $C_2$–$C_8$-alkylene, $R^3$, $R^6$ and $R^7$, which can be identical or different, are $C_1$–$C_6$-alkyl, phenyl or phenyl-$C_1$–$C_4$-alkyl, $R^4$ and $R^5$, which can be identical or different, are H or $C_1$–$C_6$-alkyl, o is 1, 2 or 3, and $X^-$ is chloride, bromide, iodide, $C_1$–$C_6$-alkylsulfate or $SO_4^{2-}/_2$. Particular preference is given to N-($C_1$–$C_6$-alkyl)diethanolamines, such as methyldiethanolamine.

Further suitable components d) are mixtures comprising at least one of the abovementioned anionic or anionogenic components and at least one of the abovementioned cationic or cationogenic components. In that case preference is given to using mixtures comprising dimethylolpropanoic acid and N-methyldiethanolamine.

Component e) comprises customary aliphatic, cycloaliphatic and/or aromatic diisocyanates, such as tetramethylene diisocyanate, hexamethylene diisocyanate, methylenediphenyl diisocyanate, 2,4- and 2,6-tolylene diisocyanate and isomer mixtures thereof, o- and m-xylylene diisocyanate, 1,5-naphthylene diisocyanate, 1,4-cyclohexylene diisocyanate, dicyclohexylmethane diisocyanate and mixtures thereof, especially isophorone diisocyanate and/or dicyclohexylmethane diisocyanate. If desired, up to 3 mol % of these compounds may be replaced by triisocyanates.

The polyurethane prepolymers A) are prepared by reaction of the compounds of components a), b) and, if used, c) and/or d) with component e). The temperature in this case lies within a range from about 60 to 140° C., preferably from about 70 to 100° C. The reaction can take place without solvent or in a suitable inert solvent or solvent mixture. Suitable solvents are aprotic polar solvents, examples being tetrahydrofuran, ethyl acetate, N-methylpyrrolidone, dimethylformamide and, preferably, ketones, such as acetone and methyl ethyl ketone. The reaction preferably takes place under an inert gas atmosphere, such as under nitrogen, for example. The components are preferably employed in amounts such that the ratio of NCO equivalent of the compounds of component e) to equivalent of active hydrogen atom of components a), b) and, if present, c) and d) lies within a range from about 1.0:1 to 1.4:1, preferably from 1.03:1 to 1.3:1 and, in particular, from 1.05:1 to 1.25:1. The resulting polyurethane prepolymers A) therefore still have free isocyanate groups.

Preferably, the polyurethane prepolymers A) comprise in copolymerized form from 0.3 to 15% by weight, preferably from 0.5 to 12% by weight, of at least one component a), from 0.5 to 80% by weight, preferably from 1 to 65% by weight, of at least one component b), from 0 to 30% by weight of at least one component c), from 0 to 25% by weight of at least one component d), from 25 to 60% by weight, preferably from 35 to 53% by weight, of at least one component e).

Polysiloxane-containing polyurethane prepolymers preferably comprise from 0.1 to 25% by weight, in particular from 0.2 to 20% by weight and, especially, from 0.3 to 15% by weight of at least one component c) in copolymerized form, based on the overall amount of components a) to e).

Where the polyurethane prepolymers comprise at least one compound d) having at least one ionogenic and/or ionic group per molecule, this compound is preferably present in copolymerized form in an amount of from 5 to 25% by weight, with particular preference from 8 to 20% by weight, based on the overall amount of components a) to e).

Polymer B)

The preparation of the crosslinked, water-soluble or water-dispersible polyurethanes employed in the compositions of the invention takes place by reacting at least one polyurethane prepolymer A), as described above, with at least one polymer B).

The polymer B) is preferably selected from

B1) addition polymers comprising in copolymerized form at least one α,β-ethylenically unsaturated monomer which additionally comprises at least one isocyanate-reactive group per molecule, B2) polyesters, B3) silicone-poly(alkylene oxide) copolymers, and mixtures thereof.

Preferred polymers B1) comprise:

f), at least one α,β-ethylenically unsaturated monomer which additionally comprises at least one isocyanate-reactive group per molecule, g) if desired, at least one α,β-ethylenically unsaturated monomer selected from esters of α,β-ethylenically unsaturated mono- and/or dicarboxylic acids with $C_1$–$C_{22}$-alkanols, amides of α,β-ethylenically unsaturated mono and/or dicarboxylic acids with mono- and di-$C_1$–$C_{22}$-alkylamines, esters of vinyl alcohol and allyl alcohol with $C_1$–$C_{40}$ monocarboxylic acids, vinyl ethers, vinylaromatic compounds, vinyl halides, vinylidene halides, $C_2$–$C_8$ monoolefins, nonaromatic hydrocarbons having at least two conjugated double bonds, and mixtures thereof, h) if desired, at least one α,β-ethylenically unsaturated monomer selected from N-vinylamides, N-vinyllactams, primary amides of α,β-ethylenically unsaturated monocarboxylic acids, vinyl- and allyl-substituted heteroaromatic compounds, and mixtures thereof, i) if desired, at least one further monomer having a free-radically polymerizable α,β-ethylenically unsaturated double bond and at least one ionogenic and/or ionic group per molecule in copolymerized form.

Suitable monomers f) are the esters of α,β-ethylenically unsaturated mono- and dicarboxylic acids, such as acrylic, methacrylic, fumaric, maleic, itaconic and crotonic acid, etc., with $C_1$–$C_{20}$-alkanediols. Examples include 2-hydroxyethyl acrylate, 2-hydroxyethyl methacrylate, 2-hydroxyethyl ethacrylate, 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, etc. It is preferred to use hydroxyethyl acrylate and hydroxyethyl methacrylate. Other suitable monomers f) are the esters of the abovementioned acids with triols and polyols such as, for example, glycerol, erythritol, pentaerythritol, sorbitol, etc.

Further suitable monomers f) are the esters and amides of the abovementioned α,β-ethylenically unsaturated mono- and dicarboxylic acids with $C_2$–$C_{12}$ amino alcohols having a primary or secondary amino group. They include aminoalkyl acrylates and aminoalkyl methacrylates and their N-monoalkyl derivatives which carry, for example, a N—$C_1$–$C_8$-monoalkyl radical, such as aminomethyl acrylate, aminomethyl methacrylate, aminoethyl acrylate, aminoethyl methacrylate, N-methylamino methylacrylate, N-methylaminomethyl methacrylate, N-ethylaminomethyl acrylate, N-ethylaminomethyl methacrylate, N-(n-propyl) aminomethyl(meth)acrylate, N-isopropylaminomethyl (meth)acrylate and, preferably, tert-butylaminoethyl acrylate and tert-butylaminoethyl methacrylate. They also include N-(hydroxy-$C_1$–$C_{12}$-alkyl)(meth)acrylamides, such as N-hydroxymethyl(meth)acrylamide, N-hydroxyethyl(meth) acrylamide, etc.

Suitable monomers f) also include the amides of the abovementioned α,β-ethylenically unsaturated mono- and dicarboxylic acids with di- and polyamines having at least two primary or two secondary or one primary and one secondary amino group(s). Examples of these include the corresponding amides of acrylic and methacrylic acid (referred to below by the use of the device "(meth)acryl . . . "), such as aminomethyl(meth)acrylamide, aminoethyl(meth)acrylamide, aminopropyl(meth) acrylamide, amino-n-butyl(meth)acrylamide, methylaminoethyl(meth)acrylamide, ethylaminoethyl(meth) acrylamide, methylaminopropyl(meth)acrylamide, ethylaminopropyl(meth)acrylamide, methylamino-n-butyl (meth)acrylamide, etc.

Suitable monomers g) are essentially hydrophobic, nonionic monomers. They include the esters of α,β-ethylenically unsaturated mono- and dicarboxylic acids with $C_1$–$C_{22}$-alkanols, preferably $C_1$–$C_{18}$-alkanols, examples being the esters of acrylic and/or methacrylic acid with methanol, ethanol, n-propanol, isopropanol, n butanol, sec-butanol, tert-butanol, n-pentanol, n-hexanol, n-heptanol, n-octanol, 2-ethylhexanol, dodecanol, hexadecanol, octadecanol, etc.

Other suitable monomers g) are amides of α,β-ethylenically unsaturated mono- and dicarboxylic acids with mono- and dialkylamines which have 1 to 22, preferably 1 to 18, carbon atoms per alkyl radical. Examples include N—$C_1$–$C_{22}$-alkyl(meth)acrylamides, such as N-methyl (meth)acrylamide, N-ethyl(meth)acrylamide, N-(n-propyl) (meth)acrylamide, N-isopropyl(meth)acrylamide, N-butyl (meth)acrylamide, N-(t-butyl)(meth)acrylamide, N-pentyl (meth)acrylamide, N-hexyl(meth)acrylamide, N-heptyl (meth)acrylamide, N-octyl(meth)acrylamide, N-ethylhexyl (meth)acrylamide, N,N-dimethyl(meth)acrylamide, N,N-diethyl(meth)acrylamide, etc.

Further suitable monomers g) are vinyl formate, vinyl acetate, vinyl propionate, vinyl n-butyrate, vinyl stearate, vinyl laurate, styrene, α-methylstyrene, o-chlorostyrene, vinyltoluenes, vinyl chloride, vinylidene chloride, ethylene, propylene, butadiene, isoprene, chloroprene, methyl, ethyl, butyl and dodecyl vinyl ethers, etc.

Suitable monomers h) are essentially hydrophilic, nonionic monomers. They include, for example, N-vinyl amides, such as N-vinylformamide, N-vinylacetamide, N-vinyl propionamide, etc. Preference is given to the use of N-vinylformamide.

Further suitable monomers h) are N-vinyllactams and their derivatives, which may, for example, have one or more $C_1$–$C_6$-alkyl substituents, such as methyl, ethyl, n-propyl, isopropyl, n-butyl, sec-butyl, tert-butyl, etc. Examples include N-vinylpyrrolidone, N-vinylpiperidone, N-vinylcaprolactam, N-vinyl-5 methyl-2-pyrrolidone, N-vinyl-5-ethyl-2-pyrrolidone, N-vinyl-6-methyl-2-piperidone, N-vinyl-6-ethyl-2 piperidone, N-vinyl-7-methyl-2-caprolactam, N-vinyl-7-ethyl-2-caprolactam, etc.

Further suitable monomers h) are primary amides of the abovementioned α,β-ethylenically unsaturated monocarboxylic acids, such as acrylamide, methacrylamide, ethacrylamide, etc.

Additional suitable monomers h) are vinyl- and allyl-substituted heteroaromatic compounds, such as 2- and 4-vinylpyridine and 2- and 4-allylpyridine, and, preferably, N-vinylheteroaromatic compounds, such as N-vinylimidazole, N-vinyl-2-methylimidazole, etc.

The compounds i) have at least one ionogenic and/or ionic group per molecule, which is preferably selected from carboxylate groups and/or sulfonate groups and the salts thereof obtainable by full or partial neutralization with a base, and also tertiary amine groups, which may be fully or partly protonated and quaternized. Suitable bases for the neutralization and, respectively, acids for the protonation and alkylating agents for the quaternization are the bases and acids specified below following the preparation of the polyurethanes of the invention.

Examples of suitable monomers i) are the abovementioned α,β-ethylenically unsaturated mono- and/or dicarboxylic acids and their monoesters and anhydrides, such as acrylic acid, methacrylic acid, fumaric acid, maleic acid, itaconic acid, crotonic acid, maleic anhydride, monobutyl maleate, etc. Preference is given to the use of acrylic acid, methacrylic acid and their alkali metal salts, such as their sodium and potassium salts.

Other suitable monomers i) are acrylamidoalkanesulfonic acids and their salts, such as 2-acrylamido-2-methylpropanesulfonic acid and its alkali metal salts, examples being its sodium and potassium salts.

Other suitable compounds i) are the esters of the abovementioned α,β-ethylenically unsaturated mono- and dicarboxylic acids with $C_2$–$C_{12}$ amino alcohols that are $C_1$–$C_8$-dialkylated on the amine nitrogen. Examples include N,N-dimethylaminomethyl(meth)acrylate, N,N-dimethylaminoethyl-(meth)acrylate, N,N-diethylaminoethyl (meth)acrylate, N,N-dimethylaminopropyl(meth)acrylate, N,N-diethylaminopropyl(meth)acrylate, etc. Preference is given to the use of N,N-dimethylaminopropyl acrylate and N,N-dimethylaminopropyl methacrylate.

Additional suitable monomers i) are the amides of the abovementioned α,β-ethylenically unsaturated mono- and dicarboxylic acids with diamines having a tertiary and a primary or secondary amino group. Examples include N-[2-(dimethylamino)ethyl]acrylamide, N-[2-(dimethylamino) ethyl]methacrylamide, N-[3-(dimethylamino)propyl] acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, etc.

In addition to component f) the polymer B1) preferably comprises at least one component g) and/or h) and, if desired, a component i) in copolymerized form.

The polymer B1) preferably comprises
from 0.05 to 15% by weight, preferably from 0.1 to 10% by weight, of at least one component f),
from 0 to 99.9% by weight of at least one component g),
from 0 to 99.9% by weight of at least one component h),
from 0 to 50% by weight, preferably from 0.1 to 46% by weight, of at least one component i),
in copolymerized form.

Preferably, the overall amount of components g) and h) lies within a range from 30 to 99.9% by weight, in particular from 40 to 99.5% by weight and, especially, from 50 to 99.5% by weight.

In one preferred embodiment the polymer B1) comprises
from 0.1 to 10% by weight, preferably from 0.5 to 5% by weight, of at least one component f),
from 50 to 99.9% by weight, preferably from 60 to 99.5% by weight, of at least one component h),
from 0 to 40% by weight, preferably from 0 to 35% by weight, of at least one component i)
in copolymerized form.

In another preferred embodiment the polymer B1) comprises
from 0.1 to 10% by weight, preferably from 0.5 to 5% by weight, of at least one component f),
from 50 to 99.9% by weight, preferably from 60 to 90% by weight, of at least one component g),
from 0 to 50% by weight, preferably from 10 to 46% by weight, of at least one component i)
in copolymerized form.

In a further preferred embodiment the polymer B1) comprises
from 0.1 to 10% by weight, preferably from 0.5 to 5% by weight, of at least one component f),
from 0.1 to 99.9% by weight, preferably from 0.1 to 90% by weight, of at least one component g),
from 0.1 to 99.9% by weight, preferably from 0.1 to 99.5% by weight, of at least one component h),
from 0 to 50% by weight, preferably from 0 to 46% by weight, of at least one component i)
in copolymerized form.

The preparation of the polymers B1) takes place in accordance with customary techniques known to the skilled worker. These include bulk polymerization and, preferably, solution polymerization. The polymerization temperature is generally from 30 to 120° C., preferably from 40 to 100° C. The polymerization medium can consist either of an organic solvent or of mixtures of water and at least one water-miscible organic solvent. Examples of preferred organic solvents are alcohols, such as methanol, ethanol, n-propanol, isopropanol and n-butanol, ketones, such as acetone and methyl ethyl ketone, tetrahydrofuran, etc. The solution polymerization can be conducted either as a batch process or in the form of a feed process, including monomer feed, staged and gradient procedures. Preference is generally given to the feed process, in which, if desired, a portion of the polymerization mixture is introduced as an initial charge and is heated to the polymerization temperature and then the remainder of the polymerization mixture, usually by way of one or more spatially separate feed ports, is supplied to the polymerization zone continuously, in stages or under a concentration gradient, while the polymerization is maintained.

Suitable initiators for the free-radical polymerization are azo compounds suitable for free-radical polymerization. They include aliphatic or cycloaliphatic azo compounds, e.g., 2,2'-azobis(isobutyronitrile), 2,2'-azobis(2-methylbutyronitrile), 2,2'-azobis(2,4-dimethylvaleronitrile), 1,1'-azobis(1-cyclohexanecarbonitrile), 2-(carbamoylazo) isobutyronitrile, 4,4'-azobis(4-cyanovaleric acid) and the alkali metal salts and ammonium salts thereof, for example, the sodium salt, dimethyl 2,2'-azobisisobutyrate, 2,2'-azobis [2-(2-imidazolin-2-yl)propane], 2,2'-azobis(2-amidinopropane), and the acid addition salts of the two latter compounds, examples being the dihydrochlorides.

Other suitable initiators are hydrogen peroxide, hydroperoxides in combination with reducing agents, and persalts. Examples of suitable hydroperoxides are t-butyl hydroperoxide, t-amyl hydroperoxide, cumene hydroperoxide and pinane hydroperoxide, in each case in combination with, for example, a salt of hydroxymethanesulfinic acid, an iron(II) salt, or ascorbic acid. Particularly suitable persalts are alkali metal peroxodisulfates.

The amount of initiator used, based on the monomers, lies generally within a range from about 0.02 to 15 mol %, preferably from 0.05 to 3 mol %.

Where relatively low molecular weights are desired they can be established by adding a regulator to the polymerization mixture. Examples of suitable regulators are aldehydes, such as formaldehyde, acetaldehyde, propionaldehyde, n-butyraldehyde and isobutyraldehyde, formic acid, ammonium formate, hydroxylammonium sulfate and hydroxylammonium phosphate. It is also possible to employ regulators containing sulfur in organically bonded form, such as di-n-butyl sulfide, di-n-octyl sulfide, diphenyl sulfide, etc., or regulators containing sulfur in the form of SH groups, such as n-butyl mercaptan, n-hexyl mercaptan or n-dodecyl mercaptan. Also suitable are water-soluble sulfur-containing polymerization regulators, such as hydrogen sulfites and disulfites, for example. Other suitable regulators include allyl compounds, such as allyl alcohol or allyl bromide, benzyl compounds, such as benzyl chloride, or alkyl halides, such as chloroform or tetrachloromethane.

If desired, following the polymerization reaction, one or more polymerization initiators are added to the polymer solution and it is heated at, for example, the polymerization temperature or at temperatures above the polymerization temperature, in order to complete the polymerization. Suitable initiators are the abovementioned azo initiators but also all other customary initiators suitable for free-radical polymerization in aqueous solution, examples being peroxides, hydroperoxides, peroxodisulfates, percarbonates, peroxo esters and hydrogen peroxide. By this means the polymerization reaction is taken to a relatively high degree of conversion, such as 99.9%, for example. The solutions resulting from the polymerization can, if desired, be converted into solid powders by a prior art drying technique. Examples of preferred techniques are spray drying, spray fluidized-bed drying, roller drying and belt drying. It is also possible to employ freeze drying and freeze concentration. If desired, the solvent can also be removed by customary methods, such as by distillation under reduced pressure, in part or in whole, and, if desired, can be exchanged for the solvent employed for the following reaction of the polymer B1) with the polyurethane prepolymer A). In this case it is preferred for hydroxyl-containing polymers B1) which have been prepared in a solvent containing active hydrogen atoms to be dried prior to the reaction with A) and subsequently to be employed in a solvent or solvent mixture which contains no active hydrogen atoms.

Component B2) is preferably a polyester based on an aromatic dicarboxylic acid or on an aromatic dicarboxylic anhydride, as are described in DE-A-26 37 167, EP-A-000 171 and, in particular, in DE-A-42 24 761, incorporated fully herein by reference. In particular, component B2) is a polyester based on a polyesterdiol having a number-average molecular weight of from 500 to 1000 and on an aromatic di- or polycarboxylic acid or on an anhydride thereof, preferably trimellitic anhydride. Preferred diols for preparing the polyesterdiol component are the diols, polyesterdiols and polyetherols specified above as components a) and b). Preferred carboxylic acid components of the polyesterdiols are aromatic dicarboxylic acids, such as phthalic, isophthalic and terephthalic acid.

Component B3) is preferably a compound of the formula II

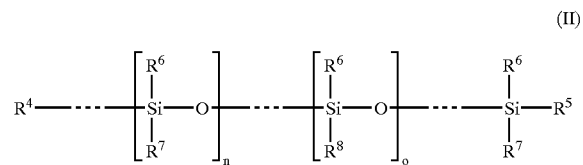

where n and o independently of one another are an integer from 0 to 200, the sum of n and o being $\geq 3$, $R^4$, $R^5$ and $R^8$ independently of one another are $C_1$–$C_8$-alkyl, benzyl, phenyl or a radical of the formula III

—(CH$_2$)$_r$—O—(CH$_2$CH$_2$O)$_p$(CH$_2$CH(CH$_3$)O)$_q$—H    (III)

in which the sequence of the alkylene oxide units III is arbitrary, r is an integer from 1 to 8, p and q independently of one another are an integer from 0 to 200, the sum of p and q being >0, $R^6$ and $R^7$ independently of one another are $C_1$–$C_8$-alkyl, benzyl or phenyl, and the compound of the formula II includes at least two radicals of the formula III.

The sum of n and o is preferably chosen such that the molecular weight of the compound of the formula II lies within a range from about 300 to 30,000.

The overall number of alkylene oxide units of the compound of the formula II, i.e., the sum of p and q in the formulae III, lies preferably within a range from about 3 to 200, preferably from 5 to 180.

The radicals $R^6$ and $R^7$ independently of one another are preferably selected from methyl, ethyl, n-propyl, isopropyl, n-butyl, sec-butyl, tert-butyl, pentyl, isopentyl, hexyl, octyl, 2-ethylhexyl, decyl, dodecyl and octadecyl, cyclohexyl, phenyl, naphthyl, benzyl, phenylethyl, tolyl and xylyl, etc.

Preferably, at least one of the radicals $R^4$ and $R^5$, with particular preference both radicals $R^4$ and $R^5$, is or are methyl.

Suitable polymers B3) are silicone-poly(alkylene oxide) copolymers, which are known under the international non-proprietary name dimethicone, the Tegopren® grades from Goldschmidt, Belsil® 6031 from Wacker, and Silvet® L from Witco.

The polyurethanes of the invention are prepared by reacting the polyurethane prepolymer A) with the polymer B). In this case the ratio of NCO equivalent of component A) to equivalent of active hydrogen atom of component B) lies in general within a range from about 20:1 to 1:1, preferably from 10:1 to 1:1 and, in particular, from 10:1 to 1.01:1. The temperature during the reaction lies in general within a range from about 10 to 150° C., preferably from about 20 to 90° C. The reaction can preferably be carried out in a suitable inert solvent or solvent mixture. Suitable solvents are those mentioned above for the preparation of the polyurethane prepolymers A). If a hydroxyl-containing polymer B1) or B3), or a hydroxyl- or carboxyl-containing polyester B2) is employed as component B) the reaction temperature is preferably within a range from about 60 to 150° C. In that case the reaction takes place preferably in a solvent or solvent mixture containing no active hydrogen atoms. Preference is given to the use of ketones, such as acetone, methyl ethyl ketone, and mixtures thereof. If use is made as component B) of a polymer B1) whose isocyanate-reactive groups are predominantly or exclusively primary and/or secondary amino groups the reaction temperature lies preferably within a range from about 20 to 80° C. In that case the reaction can, if desired, be carried out in a solvent or solvent mixture which may have active hydrogen atoms. In addition to the abovementioned compounds, in that case preferably alcohols, such as methanol and ethanol, mixtures of alcohols and water, and mixtures of a alcohols and the abovementioned ketones are employed. To prepare the polyurethanes of the invention it is preferred to introduce a solution of one of components A) or B) as initial charge to a customary reactor known to the skilled worker, an example being a stirred reactor. The second component is then added, preferably likewise in the form of a solution, and following the end of the addition the reaction is continued until the NCO content of the mixture remains constant. If the resulting polyurethanes still have free isocyanate groups, these are, finally, deactivated by adding amines, preferably amino alcohols. Suitable amino alcohols are those described above, preferably 2-amino-2-methyl-1-propanol.

The polyurethanes which contain acid groups can be partially or completely neutralized with a base. The polyurethanes which contain amine groups can be partially or completely protonated or quaternized.

As a general rule, the resulting salts of the polyurethanes are more water-soluble or dispersible in water than the non-neutralized polyurethanes. The base used to neutralize the polyurethanes can comprise alkali metal bases, such as sodium hydroxide solution, potassium hydroxide solution, sodium carbonate, sodium hydrogen carbonate, potassium carbonate or potassium hydrogen carbonate, and alkaline earth metal bases, such as calcium hydroxide, calcium oxide, magnesium hydroxide or magnesium carbonate, and also ammonia and amines. Examples of suitable amines are $C_1$–$C_6$-alkylamines, preferably n-propylamine and n-butylamine, dialkylamines, preferably diethylpropylamine and dipropylmethylamine, trialkylamines, preferably triethylamine and triisopropylamine, $C_1$–$C_6$-alkyldiethanolamines, preferably methyl- or ethyldiethanolamine, and di-$C_1$–$C_6$-alkylethanolamines. Bases which have proven particularly suitable for use in hair treatment compositions for neutralizing the polyurethanes which contain acid groups are 2-amino-2-methyl-1-propanol, diethylaminopropylamine and triisopropanolamine. Neutralization of the polyurethanes which contain acid groups can also be performed with the aid of mixtures of two or more bases, such as mixtures of sodium hydroxide solution and triisopropanolamine, for example. Depending on the end use, neutralization can be carried out partially, to the extent of from 20 to 40%, for example, or completely, i.e. 100%.

The polyurethanes containing amine groups and/or protonated or quaternized amine groups are, on the basis of their cationic groups, generally readily soluble in water or water/alcohol mixtures, or at least dispersible therein without the aid of emulsifiers. Charged cationic groups can be generated from the tertiary amine nitrogens present either by protonation with, for example, carboxylic acids, such as lactic acid, or mineral acids, such as phosphoric, sulfuric and hydrochloric acid, or by quaternization with, for example, alkylating agents, such as $C_1$–$C_4$-alkyl halides or $C_1$–$C_4$-alkyl sulfates. Examples of such alkylating agents are ethyl chloride, ethyl bromide, methyl chloride, methyl bromide, dimethyl sulfate and diethyl sulfate.

In accordance with one suitable embodiment the polyurethanes can include acid groups as well as amino groups. The difference in the amounts of acid groups and amino groups ($|\Delta AN\text{-}AmN|$) here is preferably within a range from about 15 to 150, preferably from 30 to 100. In this context, acid number (AN) and amine number (AmN) are each defined as mg of KOH/g of test substance.

Where a water-miscible organic solvent is used in preparing the polyurethanes it can be removed subsequently by customary techniques known to the skilled worker, such as by distillation under reduced pressure. In addition, water can be added to the polyurethane before the solvent is separated off. Replacing the solvent by water gives a solution or dispersion of the polymer from which, if desired, the polymer can be obtained in a customary manner, for example, by spray drying.

The polyurethanes employed in the compositions of the invention have a siloxane content, based on the overall weight of the incorporated components and corresponding to the proportion by weight of the incorporated compounds of the formulae I and/or II, of from about 0.05 to 30% by weight, preferably from 0.05 to 25% by weight, in particular from 0.05 to 20% by weight and, especially, from 0.1 to 20% by weight. Their K values (measured in accordance with E. Fikentscher, Cellulose-Chemie 13 (1932), 58–64, on a 1% strength solution in N-methylpyrrolidone) lie generally within a range from about 15 to 90, preferably from 20 to 60. Their glass transition temperature is generally at least 0° C., preferably at least 20° C., with particular preference at least 25° C. and, especially, at least 30° C. Where the polyurethanes of the invention have two or more glass transition temperatures, at least one of them lies within the stated range. The other(s) is (are) then preferably below the abovementioned temperature range.

Compositions comprising at least one polyurethane having a siloxane content in the range from 5 to 25% by weight, preferably from 7 to 20% by weight, are of preferential suitability as solubilizers for hydrophobic products, especially silicones, and as additives for hair treatment compositions. Compositions comprising at least one polyurethane having a siloxane content in the range from about 0.05 to 15% by weight are preferably employed in the form of a hair treatment composition, especially in the form of a hairspray.

The polyurethanes present in the compositions of the invention are suitable for use as auxiliaries in cosmetology and pharmacy, especially as or in coating compositions for keratinous surfaces (hair, skin and nails) and as coating compositions and/or binders for solid drug forms. Furthermore, they can be used as or in coating compositions for the textile, paper, printing, leather and adhesives industry. They are particularly suitable for use in hair cosmetics. The abovementioned polyurethanes can also be used in creams and as tablet coating and tablet binding agents. They are also suitable as binders and adhesives for cosmetic products in connection, for example, with the preparation of cosmetic products in stick form, such as stick deodorants, make-up sticks, etc.

The cosmetic compositions of the invention are particularly suitable as compositions for coating keratinous surfaces (hair, skin and nails). The compounds employed in them are soluble or dispersible in water. Where the compounds employed in the compositions of the invention are dispersible in water, they can be applied in the form of aqueous microdispersions having particle diameters of usually from 1 to 250 nm, preferably from 1 to 150 nm. In this case the solids contents of the preparations are usually within a range from about 0.5 to 20% by weight, preferably from 1 to 12% by weight. In general, these microdispersions do not require stabilization by emulsifiers or surfactants.

With preference, the compositions of the invention can be in the form of a hair treatment composition, especially in the form of a hairspray. For use as hairsetting agents, preferred compositions are those comprising polyurethanes having at least a glass transition temperature $T_g \geqq 20°$ C., preferably $\geqq 30°$ C. The K value of these polymers is preferably within a range from 23 to 90, in particular from 25 to 60.

In general, the compositions of the invention comprise the polyurethanes in an amount within the range from 0.2 to 20% by weight, based on the overall weight of the composition.

The compositions are preferably hair treatment compositions, and are usually in the form of an aqueous dispersion or in the form of an alcoholic or aqueous-alcoholic solution. Examples of suitable alcohols are ethanol, propanol, isopropanol, etc.

In addition, the hair treatment compositions of the invention generally include customary cosmetic auxiliaries, examples being softeners, such as glycerol and glycol; emollients; perfumes; UV absorbers; colorants; thickeners; antistatic substances; combability improvers; preservatives; and antifoams.

When formulated as hairsprays, the novel compositions comprise a sufficient amount of a propellant: for example, a low-boiling hydrocarbon or ether, such as propane, butane, isobutane or dimethyl ether. As propellant it is also possible to use compressed gases, such as nitrogen, air or carbon dioxide. The amount of propellant can be kept low so as not unnecessarily to raise the VOC content. In general said amount is not more than 55% by weight, based on the overall weight of the composition. However, higher VOC contents of 85% by weight or more are also possible if desired.

The polyurethanes described above can also be employed in the compositions in combination with other hair polymers. Such polymers are, in particular:

nonionic, water-soluble or water-dispersible polymers or oligomers, such as polyvinylcaprolactam, e.g. Luviskol Plus (BASF), or polyvinylpyrrolidone and its copolymers, especially with vinyl esters such as vinyl acetate, e.g. Luviskol VA 37 (BASF); polyamides, for example those based on itaconic acid and aliphatic diamines;

amphoteric or zwitterionic polymers, such as the octylacrylamide/methyl methacrylate/tert-butylaminoethyl methacrylate/2-hydroxypropyl methacrylate copolymers obtainable under the designations Amphomer® (Delft National), and zwitterionic polymers as disclosed, for example, in German Patent Applications DE 39 29 973, DE 21 50 557, DE 28 17 369 and DE 37 08 451. Acrylamido-propyltrimethylammonium chloride/acrylic acid and/or methacrylic acid copolymers, and the alkali metal salts and ammonium salts thereof, are preferred zwitterionic polymers. Suitable zwitterionic polymers are also methacryloylethyl betaine/methacrylate copolymers, which are obtainable commercially under the designation Amersette® (AMERCHOL), and copolymers of hydroxyethyl methacrylate, methyl methacrylate, N,N-dimethylaminoethyl methacrylate and acrylic acid (Jordapon®);

anionic polymers, such as vinyl acetate/crotonic acid copolymers, as are commercially available, for example, under the designations Resyn® (NATIONAL STARCH), Luviset® (BASF) and Gafset® (GAF), vinylpyrrolidone/vinyl acrylate copolymers, obtainable for example under the trademark Luviflex® (BASF). A preferred polymer is the vinylpyrrolidone/acrylate terpolymer obtainable under the designation Luviflex® VBM-35 (BASF), acrylic acid/ethyl acrylate/N-tert-butylacrylamide terpolymers, which are marketed, for example, under the designation Ultrahold® strong (BASF), and Luvimer® (BASF, terpolymer of t-butyl acrylate, ethyl acrylate and methacrylic acid), or cationic (quaternized) polymers, e.g. cationic polyacrylate copolymers based on N-vinyllactams and derivatives thereof (N-vinylpyrrolidone, N-vinylcaprolactam etc.) and also customary cationic hair conditioner polymers, e.g. Luviquat® (copolymer of vinylpyrrolidone and vinylimidazolium methochloride), Luviquat® Hold (copolymer of quaternized N-vinylimidazole, N-vinylpyrrolidone and N-vinylcaprolactam), Merquat® (polymer based on dimethyldiallylammonium chloride), Gafquat® (quaternary polymers formed by reacting polyvinylpyrrolidone with quaternary ammonium compounds), Polymer JR (hydroxyethylcellulose with cationic groups), polyquaternium types (CTFA names) etc.;

nonionic, siloxane-containing, water-soluble or -dispersible polymers, e.g. polyether siloxanes, such as Tegopren® (Goldschmidt) or Belsil® (Wacker).

The crosslinked siloxane-functional polyurethanes of the invention can be employed as a mixture with another, siloxane-free amido-functional hair polymer. Such polymers include, for example, the polyurethanes described in DE-A-42 25 045, the above-described vinylpyrrolidone/acrylate terpolymers and acrylic acid/ethyl acrylate/N-tert-butylacrylamide terpolymers (e.g. Ultrahold®strong from BASF AG), the cationic polyurethanes described in DE-A-42 41 118, the above-described amido-functional amphoteric polymers (e.g. Amphomer®) and, in particular, copolymers having a content of amido-functional monomers, such as N-vinyllactams, of at least 30% by weight (e.g. Luviskol®plus and Luviskol®VA37 from BASF AG).

The other hair polymers are preferably present in amounts of up to 10% by weight, based on the overall weight of the composition.

A preferred hair treatment composition comprises:
a) from 0.5 to 20% by weight of at least one polyurethane which is dispersible or soluble in water and comprises siloxane,
b) from 40 to 99% by weight, preferably from 50 to 98% by weight, of a solvent selected from water and water-miscible solvents, preferably $C_2$ to $C_5$ alcohols, especially ethanol, and mixtures thereof,
c) from 0 to 50% by weight of a propellant, preferably dimethyl ether,
d) from 0 to 15% by weight of at least one hair polymer which is different from a) and is dispersible or soluble in water,
e) from 0 to 0.2% by weight of at least one water-insoluble silicone,
f) from 0 to 2% by weight of at least one nonionic, siloxane-containing polymer which is dispersible or soluble in water, and customary additives.

The composition of the invention may include as component d) at least one other hair polymer which is dispersible or soluble in water. The proportion of this component will then in general be from about 0.1 to 15% by weight, preferably from 0.1 to 10% by weight, based on the overall weight of the composition. In this context it is possible with preference to employ water-soluble or water-dispersible polyurethanes which contain no siloxane groups in copolymerized form.

The composition of the invention may as component e) comprise at least one water-insoluble silicone, especially a polydimethylsiloxane, e.g. the Abil® grades from Goldschmidt. The proportion of this component will then in general be from about 0.0001 to 0.2% by weight, preferably from 0.001 to 0.1% by weight, based on the overall weight of the composition.

The composition of the invention may as component f) comprise at least one nonionic, siloxane-containing, water-soluble or -dispersible polymer, selected in particular from the polyether siloxanes described above. The proportion of this component will then in general be from about 0.001 to 2% by weight, based on the overall weight of the composition.

The composition of the invention may additionally comprise, if desired, an antifoam based, for example, on silicone. The amount of the antifoam will then in general be up to about 0.001% by weight, based on the overall amount of the composition.

The compositions of the invention possess the advantage that on the one hand they give the hair the desired set and on the other hand the polymers are easy to wash out (redispersible). Furthermore, it is possible to formulate hair treatment compositions with a VOC content of less than 85% by weight, preferably less than 60% by weight, and also to prepare purely aqueous formulations, even if they are formulated as hairsprays.

The invention is elucidated further by the following nonlimiting examples.

EXAMPLES

Examples 1 to 4

Polyurethane Prepolymer Preparation

In a stirred apparatus fitted with stirrer, dropping funnel, thermometer, reflux condenser and equipment for operating under nitrogen a polyesterdiol ($M_n$=1000 g/mol, prepared from isophthalic acid, adipic acid and hexanediol), neopentyl glycol, if appropriate dimethylolpropanoic acid (Examples 1, 2 and 4) and if appropriate N-methyldiethanolamine (Example 4) in an amount in accordance with Table 1 were dissolved in methyl ethyl ketone (solids content of the resulting reaction solution about 75%) with heating at about 70° C. and with stirring. Stirring was subsequently continued while adding isophorone diisocyanate dropwise in an amount in accordance with Table 1, during which the reaction temperature rose. At an internal temperature of 85° C. the reaction mixture was then stirred until the isocyanate group content of the mixture remained virtually constant (from about 0.5 to 1%) and then was cooled to room temperature with stirring. At about 30° C. a polysiloxanediamine ($M_n$=900 g/mol, Tegomer® A-Si 2122 from Goldschmidt, in the form of an 80% strength solution in methyl ethyl ketone) was added if appropriate (Examples 1, 2 and 3) in an amount in accordance with Table 1 to the polyurethane prepolymer prepared as described above. Then the mixture was reacted for a further 30 minutes. In all cases the reaction mixture was diluted to 40% by weight with methyl ethyl ketone.

TABLE 1

| Ex. No. | Polyesterdiol[1] [mol] | Polysiloxanediamine[2] [mol] | NPG[3] [mol] | DMPA[4] [mol] | MDEA[5] [mol] | IPDI[6] [mol] | Siloxane content [% by wt.] |
|---|---|---|---|---|---|---|---|
| 1 | 0.6 | 0.2 | 1.7 | 3 | — | 6 | 6.7 |
| 2 | 0.6 | 0.7 | 1.2 | 3 | — | 6 | 20.4 |
| 3 | 1.0 | 1.0 | 1.0 | — | — | 4 | 31.1 |
| 4 | 1.2 | — | 1.4 | 2.5 | 0.5 | 6 | 0 |

[1]Polyesterdiol of isophthalic acid, adipic acid, hexanediol, $M_n$ = 1000 g/mol
[2]Polysiloxanediamine, $M_n$ = 900 g/mol (Tegomer® A-Si 2122 from Goldschmidt)
[3]NPG = neopentyl glycol
[4]DMPA = dimethylolpropanoic acid
[5]MDEA = N-methyldiethanolamine
[6]IPDI = isophorone diisocyanate

Examples 5 to 21

Preparation of the Polymer B1)

| Feed stream 1: | 300 g | of monomer mixture according to Table 2 |
| | 30 g | of solvent: |
| | | Examples 5, 6, 8–13, 17–21: ethanol |
| | | Examples 7, 14–16: ethanol/water (1:1) |
| Feed stream 2: | 0.6 g | of 2,2'-azobis(2-methylbutyronitrile) |
| | 150 g | of ethanol |
| Feed stream 3: | 3.0 g | of 2,2'-azobis(2-methylbutyronitrile) |
| | 150 g | of ethanol |

A stirred apparatus with reflux condenser and two separate feed devices was charged with 20% by weight of feed stream 1 (monomer mixture according to Table 2), 12% by weight of feed stream 2 and 120 g of ethanol and the mixture was heated to about 75° C. Following the onset of polymerization, evident from the start of an increase in viscosity, the remainder of feed stream 1 was added over the course of 4 hours and the remainder of feed stream 2 over the course of 5 hours, the internal temperature being held at about 70 to 75° C. Subsequently, feed stream 3 was added over the course of 2 hours, with the internal temperature being increased to about 80° C. After the end of the addition polymerization was continued at this temperature for about 5 hours. The resulting polymers can be used for polyurethane preparation without further measures to reduce the residual monomer content. Polymers having very low residual monomer contents are obtained if instead of feed stream 3, for example, 2,5-bis(tert-butylperoxy-2,5-dimethylhexane) (Trigonox® 101 from Akzo Nobel) in 150 g of ethanol is added to the reaction mixture over the course of 2 hours and then polymerization is continued for about 5 hours more at a temperature of about 130° C. under the autogenous pressure of the reaction mixture.

Following polymerization, the hydroxyl-containing polymers of Examples 5 to 8 are spray-dried and then 40% strength by weight solutions of these polymers in methyl ethyl ketone are prepared for the subsequent reaction.

In the case of the polymers of Examples 14 to 16 prepared in a solvent mixture of ethanol/water (1:1), the solvent is removed by distillation under reduced pressure at about 40° C., and then 40% strength by weight solutions in ethanol are prepared for the subsequent reaction.

The ethanolic solutions of the other polymers are adjusted likewise to 40% by weight by adding further ethanol.

TABLE 2

Monomer feed stream 1

| Ex. No. | VP[1] [% by wt.] | VCap[2] [% by wt.] | t.-BA[3] [% by wt.] | EHMA[4] [% by wt.] | HEMA[5] [% by wt.] | t.-BAE-MA[6] [% by wt.] | MAA[7] [% by wt.] | AMPS-Na[8] [% by wt.] | DMAPMA[9] [% by wt.] |
|---|---|---|---|---|---|---|---|---|---|
| 5  | 97 | —    | —  | —  | 3 | —   | —            | —  | —  |
| 6  | 47 | 50   | —  | —  | 3 | —   | —            | —  | —  |
| 7  | 37 | —    | 45 | —  | 3 | —   | MAA-Na[10] 15 | —  | —  |
| 8  | 47 | 42   | —  | —  | 3 | —   | —            | —  | 8  |
| 9  | 98 | —    | —  | —  | — | 2   | —            | —  | —  |
| 10 | —  | 99.5 | —  | —  | — | 0.5 | —            | —  | —  |
| 11 | —  | 69   | 30 | —  | — | 1   | —            | —  | —  |
| 12 | 69 | —    | 30 | —  | — | 1   | —            | —  | —  |
| 13 | 59 | —    | 35 | 5  | — | 1   | —            | —  | —  |
| 14 | —  | —    | 73 | —  | — | 2   | 25           | —  | —  |
| 15 | —  | —    | 23 | 30 | — | 2   | —            | 45 | —  |
| 16 | 74 | —    | —  | —  | — | 1   | —            | 25 | —  |
| 17 | 90 | —    | —  | —  | — | 1   | —            | —  | 9  |
| 18 | 45 | 45   | —  | —  | — | 1   | —            | —  | 9  |
| 19 | —  | 90   | —  | —  | — | 1   | —            | —  | 9  |
| 20 | —  | 90.5 | —  | —  | — | 0.5 | —            | —  | 9  |
| 21 | 45 | —    | 35 | 5  | — | 1   | —            | —  | 14 |

[1] VP = vinylpyrrolidone
[2] VCap = vinylcaprolactam
[3] t.-BA = tert-butyl acrylate
[4] EHMA = ethylhexyl methacrylate
[5] HEMA = hydroxyethyl methacrylate
[6] t.-BAEMA = tert-butylaminoethyl methacrylate
[7] MAA = methacrylic acid
[8] AMPS-Na = sodium salt of acrylamidomethylpropanesulfonic acid
[9] DMAPMA = dimethylaminopropyl methacrylate
[10] MAA-Na = sodium salt of methacrylic acid

Examples 22 and 23

Preparation of the Polyester B2)

A four-necked flask fitted with stirrer, internal thermometer, descending condenser and equipment for operating under nitrogen was charged with diethylene glycol, 1,4-cyclohexanedimethylol, polypropylene glycol ($M_n$=600 g/mol) if appropriate (Example 23) and neopentyl glycol in an amount in accordance with Table 3 and also 100 ppm of tetrabutyl orthotitanate as catalyst. Under a gentle stream of nitrogen the reaction mixture was dissolved with heating at about 80° C. and with stirring. Then an amount of isophthalic acid in accordance with Table 3 was added, after which the mixture was heated at 160° C. for 2 hours. Subsequently, the temperature was raised to 20° C./h and, at about 220° C., the water of reaction was removed by distillation until the acid number had fallen below 15. Subsequently, trimellitic anhydride was added in an amount in accordance with Table 3, 100 ppm of further catalyst were added, and the mixture was reacted further at a temperature of about 200° C. and a reduced pressure of about 10 mm Hg for 4 hours more. Cooling to about 70° C. gave a pale yellow polyester which was formulated with methyl ethyl ketone to give a 70% strength by weight solution.

TABLE 3

Polyesters B2

| Ex. No. | IPA[1] [mol] | NPG[2] [mol] | CHDM[3] [mol] | DEG[4] [mol] | PPG[5] [mol] | TMA[6] [mol] | K value[7] |
|---|---|---|---|---|---|---|---|
| 22 | 125 | 70 | 23 | 40 | —  | 25 | 24.6 |
| 23 | 125 | 70 | 23 | 40 | 7  | 25 | 25.3 |

[1] IPA = isophthalic acid
[2] NPG = neopentyl glycol
[3] CHDM = 1,4-cyclohexanedimethylol
[4] DEG = diethylene glycol
[5] PPG = polypropylene glycol; MW about 600 g/mol
[6] TMA = trimellitic anhydride
[7] determined as a 1% strength solution in N-methylpyrrolidone

Examples 24 to 28 and 46 to 48

Polyurethane Preparation

A stirred apparatus equipped with stirrer, dropping funnel, thermometer and reflux condenser was charged with a 40% strength by weight solution (in methyl ethyl ketone) of a polyurethane prepolymer from Example 1, 2 or 4, as indicated in Table 4, and this initial charge was heated to 60° C. Subsequently, in the case of Examples 24 to 28, a 40% strength by weight solution of a hydroxyl-containing polymer B1) from Examples 5 to 8, again in methyl ethyl ketone, was mixed in as indicated in Table 4. The reaction mixture was stirred at about 85° C. until the isocyanate group content of the mixture remained virtually constant (about 2 hours).

Subsequently, water was added to the reaction mixture and the reaction product was neutralized with 2-amino-2-methylpropanol (pH about 8.0). The methyl ethyl ketone was then distilled off under reduced pressure at 40° C. to give an aqueous dispersion of the polyurethane.

In the case of Examples 46 to 48 the procedure followed was similar except that instead of the hydroxyl-containing polymer B1) a silicone-poly(alkylene oxide) copolymer B3) (Belsil® 6031 from Wacker) was employed as a 40% strength by weight solution in methyl ethyl ketone.

Products in powder form can be obtained by spray drying.

Examples 29 to 43

A stirred apparatus equipped with stirrer, dropping funnel, thermometer and reflux condenser was charged with a 40% strength by weight solution of a polyurethane prepolymer from Examples 1 to 3 in methyl ethyl ketone, as per Table 4. At a temperature of about 30° C. a polymer B1) (or a mixture, Example 43), in accordance with Table 4, was then mixed in in the form of a 40% strength by weight solution in ethanol. The reaction mixture was then stirred for about 1 hour at ambient temperature. Subsequently, water was added to the reaction mixture, and the reaction product was neutralized with 2-amino-2-methylpropanol (pH about 8.0). The methyl ethyl ketone was then distilled off under reduced pressure at 40° C. to give an aqueous dispersion of the polyurethane.

A product in powder form can be obtained by spray drying.

Examples 44 and 45

A stirred apparatus equipped with stirrer, dropping funnel, thermometer and reflux condenser was charged with a 40% strength by weight solution of a polyurethane prepolymer from Example 2 or 3 in methyl ethyl ketone, as indicated in Table 4, and this initial charge was heated to 70° C. Subsequently, a 70% strength by weight solution of a polyester B2) (from Examples 22 and 23) in methyl ethyl ketone was mixed in in an amount in accordance with Table 4. The reaction mixture was stirred at about 70° C. until the isocyanate group content was equal to 0 (about 2 hours). Then free carboxyl groups still present were neutralized with 2-amino-2-methylpropanol (pH about 8.2). Subsequently, water was added to the reaction mixture, and the methyl ethyl ketone was distilled off at 40° C. with addition of one drop of silicone antifoam, to give a stable aqueous dispersion.

A product in powder form can be obtained by spray drying.

TABLE 4

| Ex. No. | PU prepolymer | | Polymer B) | | K value[1] |
|---|---|---|---|---|---|
| | Ex. No. | [% by wt.] | Ex. No. | [% by wt.] | |
| 24 | 1 | 80 | 5 | 20 | 33.0 |
| 25 | 1 | 50 | 6 | 50 | 37.3 |
| 26 | 1 | 90 | 7 | 10 | 32.4 |
| 27 | 1 | 90 | 8 | 10 | 34.7 |
| 28 | 2 | 90 | 8 | 10 | 36.1 |
| 29 | 1 | 90 | 9 | 10 | 34.7 |
| 30 | 1 | 70 | 10 | 30 | 35.4 |
| 31 | 1 | 90 | 14 | 10 | 37.6 |
| 32 | 1 | 80 | 16 | 20 | 39.4 |
| 33 | 1 | 80 | 17 | 20 | 31.2 |
| 34 | 1 | 80 | 18 | 20 | 35.3 |

TABLE 4-continued

| Ex. No. | PU prepolymer | | Polymer B) | | K value[1] |
|---|---|---|---|---|---|
| | Ex. No. | [% by wt.] | Ex. No. | [% by wt.] | |
| 35 | 1 | 70 | 20 | 30 | 32.1 |
| 36 | 1 | 80 | 21 | 20 | 37.4 |
| 37 | 2 | 80 | 18 | 20 | 32.0 |
| 38 | 1 | 10 | 21 | 90 | 46.2 |
| 39 | 1 | 20 | 10 | 80 | 42.0 |
| 40 | 1 | 30 | 20 | 70 | 41.0 |
| 41 | 3 | 10 | 14 | 90 | 39.7 |
| 42 | 3 | 10 | 17 | 90 | 43.9 |
| 43 | 3 | 10 | 13 | 30 | 40.0 |
| | | | 14 | 60 | |
| 44 | 3 | 6.67 | 22 | 93.33 | 26.2 |
| 45 | 2 | 20 | 23 | 80 | 25.8 |
| 46 | 4 | 95 | silicone | 5 | 30.2 |
| 47 | 4 | 80 | silicone | 20 | 25.2 |
| 48 | 2 | 80 | silicone | 20 | 24.7 |

[1] 1% strength by weight solution in N-methylpyrrolidone

Practical Examples

Examples 49 to 69

Aerosol hairspray formulations with a VOC content of 97% by weight:

Polyurethane of Examples

| 24–27, 29–36, 38–46 | 3.00% | by weight |
| Ethanol | 62.00% | by weight |
| Dimethyl ether | 34.96% | by weight |
| Perfume, additives | q.s. | |

Examples 70 to 90

Compact aerosol hairspray formulations with a VOC content of 90% by weight:

Polyurethane of Examples

| 24–27, 29–36, 38–46 | 10.00% | by weight |
| Ethanol | 55.00% | by weight |
| Dimethyl ether | 34.96% | by weight |
| Perfume, additives | q.s. | |

Examples 91 to 111

Hairspray formulations with a VOC content of 80% by weight:

Polyurethane of Examples

| 24–27, 29–36, 38–46 | 5.00% | by weight |
| Ethanol | 45.00% | by weight |
| Water | 15.00% | by weight |
| Dimethyl ether | 34.96% | by weight |
| Perfume, additives | q.s. | |

Examples 112 to 126

Hairspray formulations with a VOC content of 55% by weight:

Polyurethane of Examples

| | | |
|---|---|---|
| 24–27, 29–36, 44–46 | 5.00% | by weight |
| Ethanol | 20.00% | by weight |
| Water | 40.00% | by weight |
| Dimethyl ether | 34.96% | by weight |
| Perfume, additives | q.s. | |

Examples 127 to 141

Pump hairspray formulations with 0 VOC content:

Polyurethane of Examples

| | | |
|---|---|---|
| 24–27, 29–36, 44–46 | 10.00% | by weight |
| Water | 89.97% | by weight |
| Perfume, additives | q.s. | |

Film Evaluation

All of the abovementioned hairspray formulations gave clear, firm films which were good in terms of their flexibility and smoothness. The polyurethanes of Preparative Examples 28, 37, 47 and 48 with a high siloxane content give very soft and slightly tacky films. These polyurethanes are not suitable alone as hairsetting polymers, but can be formulated as an additive, with another setting polymer, to give silicone-containing hairsprays having very good properties. This is shown by the following inventive examples (L) and comparative examples (VL) 1 to 16.

Examples (V)L1 to 16

The polyurethanes from Examples 37, 47 and 48 were formulated individually and in the form of mixtures with conventional siloxane-free hairsetting polymers, with or without the addition of a water-insoluble silicone, as 5% strength by weight solutions in ethanol. The compositions of these formulations are shown in Table 6. The formulations were applied to a glass plate and the resulting films were tested for 5 criteria, which are indicated in Table 5, and given ratings from 1 to 4. The evaluations of the films are shown in Table 7.

The comparative examples used consisted firstly of pure 95% strength by weight solutions of the conventional, prior art siloxane-free hairsetting polymers which were also used to modify the siloxanes employed in accordance with the invention (VL1 to VL3). Also used as comparative examples were pure 95% strength by weight solutions of the polyurethanes of Examples 37, 47 and 48 (VL4 to VL6). A further comparative example used was a 95% strength by weight solution of a salt of a monofunctional carboxylic acid and a difunctional polydimethylsiloxanediamine (VL7) which was also used to modify the siloxanes employed in accordance with the invention.

TABLE 5

| Evaluation criteria | | Rating |
|---|---|---|
| A) Smoothness | rough | 4 |
| | moderately smooth | 3 |
| | smooth | 2 |
| | very smooth | 1 |
| B) Adhesion | poor | 4 |
| | moderate | 3 |
| | good | 2 |
| | very good | 1 |
| C) Elasticity/tackiness | brittle/slightly tacky | 4 |
| | soft/slightly tacky | 3 |
| | soft-hard/slightly tacky | 2–3 |
| | hard/non-tacky | 2 |
| | hard-elastic/non-tacky | 1–2 |
| | elastic/non-tacky | 1 |
| D) Ease of washout | poor | 4 |
| | moderate | 3 |
| | good | 2 |
| | very good | 1 |
| E) Appearance | nonuniform, cloudy | 4 |
| | nonuniform, clear | 3 |
| | uniform, clear | 2 |
| | uniform, lustrous | 1 |

TABLE 6

Inventive (L) and comparative (VL) formulations based on polyurethanes 37, 47 and 48

| | | | | Polyurethane of Preparation Example No. | | | | Poly dimethyl- |
|---|---|---|---|---|---|---|---|---|
| Polymer solution[1] | HFP1[2] [% by wt.] | HFP2[3] [% by wt.] | HFP3[4] [% by wt.] | 37 [% by wt.] | 47 [% by wt.] | 48 [% by wt.] | HFP salt[5] [% by wt.] | siloxane[6] [% by wt.] |
| VL1 | 5 | — | — | — | — | — | — | — |
| VL2 | — | 5 | — | — | — | — | — | — |
| VL3 | — | — | 5 | — | — | — | — | — |
| VL4 | — | — | — | 5 | — | — | — | — |
| VL5 | — | — | — | — | 5 | — | — | — |
| VL6 | — | — | — | — | — | 5 | — | — |
| VL7 | — | — | — | — | — | — | 5 | — |
| VL8 | 4.5 | — | — | — | — | — | 0.5 | — |
| L9 | 4.5 | — | — | — | — | 0.5 | — | — |
| L10 | — | 4.5 | — | — | 0.5 | — | — | — |
| L11 | — | — | 4.5 | 0.5 | — | — | — | — |

TABLE 6-continued

Inventive (L) and comparative (VL) formulations based on polyurethanes 37, 47 and 48

| Polymer solution[1] | HFP1[2] [% by wt.] | HFP2[3] [% by wt.] | HFP3[4] [% by wt.] | Polyurethane of Preparation Example No. | | | HFP salt[5] [% by wt.] | Poly dimethyl- siloxane[6] [% by wt.] |
|---|---|---|---|---|---|---|---|---|
| | | | | 37 [% by wt.] | 47 [% by wt.] | 48 [% by wt.] | | |
| VL12 | — | — | 5 | — | — | — | — | 0.001 |
| L13 | 4.5 | — | — | — | — | 0.5 | — | 0.001 |
| L14 | — | 4.5 | — | — | 0.5 | — | — | 0.001 |
| L15 | — | — | 4.5 | 0.5 | — | — | — | 0.001 |
| L16 | — | — | 3.5 | 1.5 | — | — | — | 0.001 |

[1] each 5% strength by weight solutions in ethanol
[2] amido-functional conventional hairsetting polymer based on N-vinyllactam (Luviskol ® VA37 from BASF AG)
[3] Hairsetting polymer based on t-butyl acrylate, ethyl acrylate and methacrylic acid (Luvimer ® 100 P from BASF AG)
[4] Polyurethane made from polyesterdiol (prepared from isophthalic acid, adipic acid and hexanediol, $M_w$ = 1000 g/mol), Dimethylolpropanoic acid and isophorone diisocyanate
[5] salt of Tegomer ® Ä-Si 2120 (from Goldschmidt) and lactic acid
[6] Abil ® 200 from Goldschmidt

TABLE 7

Film properties of the polyurethanes

| Polymer solution | Evaluation | | | | |
|---|---|---|---|---|---|
| | A | B | C | D | E |
| VL1 | 2 | 1 | 2 | 1 | 1–2 |
| VL2 | 3 | 1 | 2 | 2 | 2 |
| VL3 | 3 | 1 | 1–2 | 2 | 2 |
| VL4 | 1 | 1 | 2–3 | 2 | 1–2 |
| VL5 | 1 | 1 | 2–3 | 2 | 1–2 |
| VL6 | 1–2 | 1 | 3 | 2 | 1–2 |
| VL7 | —*) | —*) | 3 | —*) | —*) |
| VL8 | 1–2 | 3–4 | 3 | 1 | 1–2 |
| L9 | 1–2 | 1 | 2 | 1 | 1–2 |
| L10 | 2 | 1 | 2 | 2 | 2 |
| L11 | 2 | 1 | 1–2 | 2 | 1–2 |
| VL12 | 1–2 | 1 | 2 | 2–3 | 3 |
| L13 | 1 | 1 | 2 | 1 | 1–2 |
| L14 | 1–2 | 1 | 2 | 2 | 2 |
| L15 | 1 | 1 | 1–2 | 2 | 1–2 |
| L16 | 1 | 1 | 1 | 2 | 1–2 |

*) no film formed

We claim:
1. A hair treatment composition comprising, as a hair setting ingredient, an effective amount of at least one crosslinked, water-soluble or water-dispersible polyurethane or a salt thereof, which polyurethane is formed by reacting
   A) at least one polyurethane prepolymer having terminal isocyanate groups formed from
      a) at least one compound having a molecular weight in the range from 56 to 300 which comprises two active hydrogen atoms per molecule,
      b) at least one polymer having two active hydrogen atoms per molecule,
      c) optionally a polysiloxane,
      d) optionally at least one compound which has two active hydrogen atoms and at least one ionogenic or ionic group per molecule,
      e) at least one diisocyanate, and
   B) at least one polymer having isocyanate-reactive groups selected from hydroxyl, primary and secondary amino and/or carboxyl groups, where the polymer B) is selected from
      B1) polymers comprising in copolymerized form at least one α,β-ethylenically unsaturated monomer which additionally comprises at least one isocyanate-reactive group per molecule,
      B2) polyesters,
      B3) silicon-poly(alkylene oxide) copolymers,
      and mixtures thereof,
   wherein at least one of components A) and/or B) is soluble or dispersible in water and at least one of components A) and/or B) comprises at least one siloxane group, and which composition is in form of an aqueous dispersion, an alcoholic solution or an aqueous-alcoholic solution.
2. The composition defined in claim 1, where the polysiloxane is a compound of the formula I

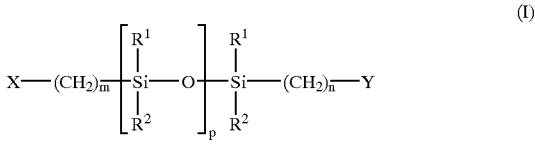

where
   $R^1$ and $R^2$ independently of one another are $C_1$- to $C_4$-alkyl, benzyl or phenyl,
   X and Y independently of one another are OH or $NHR^3$, where $R^3$ is hydrogen, $C_1$- to $C_6$-alkyl or $C_5$- to $C_8$-cycloalkyl,
   m and n independently of one another are from 2 to 8, and p is from 3 to 50.
3. The composition defined in claim 1, where the ratio of NCO equivalent of the compounds of component e) to equivalent of active hydrogen atom of components a), b), c) and d) lies within a range from 1.01:1 to 1.4:1.
4. A composition as claimed in claim 1, where the polymer B1) comprises
   f) at least one α,β-ethylenically unsaturated monomer which additionally comprises at least one isocyanate-reactive group per molecule,
   g) optionally, at least one α,β-ethylenically unsaturated monomer selected from esters of α,β-ethylenically unsaturated mono- and/or dicarboxylic acids with $C_1$–$C_{22}$-alkanols, amides of α,β-ethylenically unsaturated mono and/or dicarboxylic acids with mono- and di-$C_1$–$C_{22}$-alkylamines, esters of vinyl alcohol and allyl alcohol with $C_1$–$C_{40}$ monocarboxylic acids, vinyl ethers, vinylaromatic compounds, vinyl halides, vinylidene halides, $C_2$–$C_8$ monoolefins, nonaromatic hydrocarbons having at least two conjugated double bonds, and mixtures thereof, h) optionally, at least one α,β-ethylenically unsaturated monomer selected from N-vinylamides, N-vinyllactams, primary amides of α,β-ethylenically unsaturated monocarboxylic acids, vinyl- and allyl-substituted heteroaromatic compounds, and mixtures thereof, i) optionally, at least one further monomer having a free-radically polymerizable α,β-ethylenically unsaturated double bond and at least one ionogenic and/or ionic group per molecule in copolymerized form.

5. A composition as claimed in claim 1, where the polymer B2) is a polyester based on a polyesterdiol having a number-average molecular weight of from 500 to 1000 and on an aromatic di- or polycarboxylic acid or an anhydride thereof.

6. A composition as claimed in claim 1, where the polymer B3) is a compound of the formula II

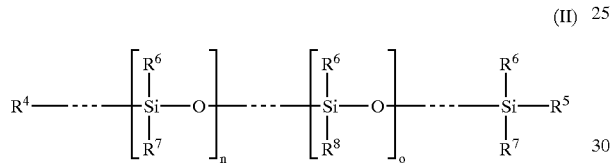

where
n and o independently of one another are an integer from 0 to 200, the sum of n and o being $\geq 3$,
$R^4$, $R^5$ and $R^8$ independently of one another are $C_1$–$C_8$-alkyl, benzyl, phenyl or a radical of the formula III $$—(CH_2)_r—O—(CH_2CH_2O)_p(CH_2CH(CH_3)O)_q—H \quad (III)$$

in which the sequence of the alkylene oxide units is arbitrary,
r is an integer from 1 to 8,
p and q independently of one another are an integer from 0 to 200, the sum of p and q being >0,
$R^6$ and $R^7$ independently of one another are $C_1$–$C_8$-alkyl, benzyl or phenyl,
and the compound of the formula II includes at least two radicals of the formula III.

7. A composition as claimed in claim 1, where the ratio of NCO equivalent of component A) to equivalent of active hydrogen atom of component B) lies within a range from 20:1 to 1:1.

8. A composition as claimed in claim 1, where the polyurethanes have a proportion of siloxane-containing compounds of formula I and/or II, formula I being

wherein
$R^1$ and $R^2$ independently of one another are $C_1$- to $C_4$-alkyl, benzyl or phenyl, X and Y independently of one another are OH or $NHR^3$, where $R^3$ is hydrogen, $C_1$- to $C_6$-alkyl or $C_5$- to $C_8$-cycloalkyl,
m and n independently of one another are from 2 to 8, and
p is from 3 to 50, and
formula II being

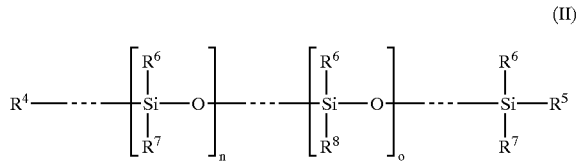

wherein
n and o independently of one another are an integer from 0 to 100, the sum of n and o being $\geq 3$,
$R^4$ and $R^5$ independently of one another are $C_1$–$C_8$-alkyl, benzyl, phenyl or a radical of formula III $$—(CH_2)_r—O—(CH_2—CH_2—O)_p(CH_2—CH(CH_3)O)_q—H \quad (III)$$

in which
r is an integer from 1 to 8,
p and q independently of one another are an integer from 0 to 200, the sum of p and q being >0, and the sequence of the alkylene oxide units is arbitrary,
$R^6$ and $R^7$ independently of one another are $C_1$–$C_8$-alkyl, benzyl or phenyl,
based on the overall weight of the incorporated components, of from 0.05 to 30% by weight.

9. A composition as claimed in claim 8, comprising at least one polyurethane having a siloxane content in the range from 0.05 to 15% by weight, in the form of a hair treatment composition.

10. A composition as claimed in claim 9 comprising
a) from 0.5 to 20% by weight of at least one polyurethane which is dispersible or soluble in water,
b) from 40 to 99% by weight, of a solvent selected from water and water-miscible solvents,
c) from 0 to 50% by weight of a propellant,
d) from 0 to 15% by weight of at least one hair polymer which is different form a) and is dispersible or soluble in water,
e) from 0 to 0.2% by weight of at least one water-insoluble silicone,
f) from 0 to 2% by weight of at least one nonionic, siloxane-containing polymer which is dispersible or soluble in water.

11. A solubilizer for hydrophobic products or additive for hair treatment compositions comprising at least one crosslinked, water-soluble or water dispersible polyurethane having a siloxane content in the range from 5 to 20% by weight, or a salt thereof, which polyurethane is formed by reacting A) at least one polyurethane prepolymer having terminal isocyanate groups formed from
a) at least one compound having a molecular weight in the range from 56 to 300 which comprises two active hydrogen atoms per molecule,
b) at least one polymer having two active hydrogen atoms per molecule,
c) optionally a polysiloxane,
d) optionally at least one compound which has two active hydrogen atoms and at least one ionogenic or ionic group per molecule,
e) at least one diisocyanate, and B) at least one polymer having isocyanate-reactive groups selected from hydroxyl, primary and secondary amino and/or carboxyl groups, where the polymer B is selected from
- B1) polymers comprising in copolymerized form at least one α,β-ethylenically unsaturated monomer which additionally comprises at least one isocyanate-reactive group per molecule,
- B2) polyesters,
- B3) silicon-poly(alkylene oxide) copolymers, and mixtures thereof, wherein at least one of components A) and/or B) is soluble or dispersible in water and at least one of components A) and/or B) comprises at least one siloxane group, and which is in form of an aqueous dispersion, an alcoholic solution or an aqueous-alcoholic solution.

12. The composition defined in claim 1, wherein compounds a) is a polyesterdiol prepared from isophthalic acid, adipioc acid and hexanediol.

13. A composition claimed in claim 5, where the aromatic dicarboxylic acid anhydride in compound a) is a polyesterdiol prepared from isophthalic acid, adipic acid and hexanediol.

* * * * *

UNITED STATES PATENT AND TRADEMARK OFFICE
CERTIFICATE OF CORRECTION

PATENT NO. : 6,579,517 B1
DATED : June 17, 2003
INVENTOR(S) : Kim et al.

It is certified that error appears in the above-identified patent and that said Letters Patent is hereby corrected as shown below:

<u>Column 30,</u>
Line 18, "$R^4$ and $R^5$" should be -- $R^4$, $R^5$ and $R^8$ --.

<u>Column 32,</u>
Line 6, "adipioc acid" should be -- adipic acid --.

Signed and Sealed this

Ninth Day of December, 2003

JAMES E. ROGAN
*Director of the United States Patent and Trademark Office*